US011583819B2

(12) United States Patent
Lopez et al.

(10) Patent No.: US 11,583,819 B2
(45) Date of Patent: Feb. 21, 2023

(54) PROGRAMMABLE LIQUID, GEL AND BIOHYBRID COMPARTMENTS AND METHODS OF USE

(71) Applicants: Duke University, Durham, NC (US); UNM Rainforest Innovations, Albuquerque, NM (US)

(72) Inventors: Gabriel P. Lopez, Durham, NC (US); Joseph R. Simon, Durham, NC (US); Nick J. Carroll, Durham, NC (US); Ashutosh Chilkoti, Durham, NC (US)

(73) Assignees: UNM Rainforest Innovations, Albuquerque, NM (US); Duke University, Durham, NC (US)

( * ) Notice: Subject to any disclaimer, the term of this patent is extended or adjusted under 35 U.S.C. 154(b) by 0 days.

(21) Appl. No.: 16/817,299

(22) Filed: Mar. 12, 2020

(65) Prior Publication Data

US 2020/0276553 A1    Sep. 3, 2020

Related U.S. Application Data

(63) Continuation of application No. 15/487,543, filed on Apr. 14, 2017, now abandoned, which is a continuation of application No. PCT/US2015/055836, filed on Oct. 15, 2015.

(60) Provisional application No. 62/064,057, filed on Oct. 15, 2014.

(51) Int. Cl.

| | |
|---|---|
| *A61K 9/14* | (2006.01) |
| *B01J 2/00* | (2006.01) |
| *C07K 14/78* | (2006.01) |
| *A61L 31/16* | (2006.01) |
| *A61L 27/34* | (2006.01) |
| *A61L 29/08* | (2006.01) |
| *A61L 31/10* | (2006.01) |
| *C12M 1/00* | (2006.01) |
| *B01J 13/06* | (2006.01) |
| *C07K 19/00* | (2006.01) |
| *A61K 38/00* | (2006.01) |
| *B01J 2/06* | (2006.01) |
| *A61L 27/54* | (2006.01) |

(52) U.S. Cl.
CPC .............. *B01J 13/06* (2013.01); *A61K 9/146* (2013.01); *A61K 38/00* (2013.01); *A61L 27/34* (2013.01); *A61L 27/54* (2013.01); *A61L 29/085* (2013.01); *A61L 31/10* (2013.01); *A61L 31/16* (2013.01); *B01J 2/00* (2013.01); *B01J 2/06* (2013.01); *C07K 14/78* (2013.01); *C07K 19/00* (2013.01); *C12M 23/20* (2013.01); *A61L 2300/62* (2013.01)

(58) Field of Classification Search
CPC .... A61L 2300/62; A61L 27/54; A61L 29/085; A61L 31/10; A61L 31/16; B01J 13/06; B01J 2/06; B01J 2/00; A61K 38/00; A61K 38/39; C07K 14/78; C07K 19/00
See application file for complete search history.

(56) References Cited

U.S. PATENT DOCUMENTS

| | | | | |
|---|---|---|---|---|
| 6,716,456 | B1 * | 4/2004 | Mapelli | ............... B01J 13/10 424/400 |
| 2008/0233199 | A1 | 9/2008 | Kumar et al. | |
| 2009/0253165 | A1 | 10/2009 | Dardelle et al. | |
| 2009/0263165 | A1 | 10/2009 | Ota | |
| 2010/0086651 | A1 * | 4/2010 | Dardelle | ............... A23L 29/281 426/89 |
| 2011/0294864 | A1 | 12/2011 | Remon et al. | |
| 2017/0216808 | A1 | 8/2017 | Lopez et al. | |

FOREIGN PATENT DOCUMENTS

WO    WO-2016061419 A1    4/2016

OTHER PUBLICATIONS

Eldijk et al. (Biomolecules 15, 2751-2759, Jun. 19, 2014). (Year: 2014).*
Nie et al. (J. Am. Chem. Soc. 2006, 128, 9408-9412). (Year: 2006).*
Huang et al. (Langmuir 2012, 28, 665-665) (Year: 2012).*
"U.S. Appl. No. 15/487,543, Advisory Action dated Mar. 14, 2019", 3 pgs.
"U.S. Appl. No. 15/487,543, Examiner Interview Summary dated Jan. 23, 2020", 2 pgs.
"U.S. Appl. No. 15/487,543, Examiner Interview Summary dated Sep. 27, 2018", 3 pgs.
"U.S. Appl. No. 15/487,543, Final Office Action dated Nov. 12, 2019", 18 pgs.
"U.S. Appl. No. 15/487,543, Final Office Action dated Dec. 31, 2018", 23 pgs.
"U.S. Appl. No. 15/487,543, Non Final Office Action dated May 23, 2019", 23 pgs.
"U.S. Appl. No. 15/487,543, Non Final Office Action dated Nov. 9, 2017", 13 pgs.
"U.S. Appl. No. 15/487,543, Notice of Non-Compliant Amendment dated Jun. 15, 2018", 5 pgs.

(Continued)

*Primary Examiner* — Anna R Falkowitz
(74) *Attorney, Agent, or Firm* — Schwegman Lundberg & Woessner, P.A.

(57) ABSTRACT

Nano- to microscale liquid coacervate particles are provided. The liquid coacervate particles are produced by a process including stimulating a population of liquid droplets containing one or a mixture of components to induce a phase separation point of a first component, and maintaining stimulation at the phase separation point to form a coacervate domain of the first component within each of the droplets to form the liquid coacervate particles. The self-assembled nano, meso, micro and macro liquid coacervate particles and related coated substrates can have utility in drug delivery, bioanalytical systems, controlled cell culture, tissue engineering, biomanufacturing and drug discovery.

22 Claims, 10 Drawing Sheets

(56) References Cited

OTHER PUBLICATIONS

"U.S. Appl. No. 15/487,543, Response filed Mar. 4, 19 to Final Office Action dated Dec. 31, 2018", 13 pgs.
"U.S. Appl. No. 15/487,543, Response filed Mar. 8, 18 to Non Final Office Action dated Nov. 9, 2017", 12 pgs.
"U.S. Appl. No. 15/487,543, Response filed Mar. 18, 19 to Advisory Action dated Mar. 14, 2019", 13 pgs.
"U.S. Appl. No. 15/487,543, Response filed Aug. 23, 19 to Non Final Office Action dated May 23, 2019", 11 pgs.
"U.S. Appl. No. 15/487,543, Response filed Sep. 11, 17 to Restriction Requirement dated Jul. 10, 2017", 7 pgs.
"U.S. Appl. No. 15/487,543, Response filed Sep. 18, 18 to Notice of Non-Compliant Amendment dated Jun. 15, 2018", 12 pgs.
"U.S. Appl. No. 15/487,543, Restriction Requirement dated Jul. 10, 2017", 13 pgs.
"International Application Serial No. PCT/US2015/055836, International Preliminary Report on Patentability dated Apr. 27, 2017", 12 pgs.
"International Application Serial No. PCT/US2015/055836, International Search Report dated Jan. 14, 2016", 3 pgs.
"International Application Serial No. PCT/US2015/055836, Written Opinion dated Jan. 14, 2016", 10 pgs.
Andersen, E S, et al., "Self-assembly of a nanoscale DNA box with a controilabie lid", Nature 459, (2009), 73-76.
Caruso, F, et al., "Protein Multilayer Formation on Colloids through a Stepwise Self-Assembly Technique", J Am Chem Soc 121 (1999), 6039-6046.
Chen. J. H., et al.. "Synthesis from DNA of a Molecule with the Connectivity of a Cube.", Nature, 350, (1991), 631-33.
Chu, L Y, et al., "Controllable Monodisperse Multiple Emulsions", Angewandte Chemie International Edition 46, (2007), 8970-8974.
Dewey, D C, et al.. "Bioreactor droplets from liposomestabilized ali-aqueous emulsions", Nat Common 5, (2014).
Dreher, M R, et al., "Temperature triggered self-assembly of polypeptides into multivalent spherical micelles", J Am Chem Soc 130, (2008), 687-694.

Eldijk, et al., Biomacromolecules, (Jun. 19, 2014), 2751-2759.
Enoch, H G, et al., "Formation and Properties of 1000-angstrom-Diameter, Single-Bilayer Phospholipid Vesicles", P Natl Acad Sci USA 76, (1979), 145-149.
Hartgerink, J D, et al., "Peptide-amphiphile nanofibers: A versatile scaffold for the preparation of Self-assembling materials", Proceedings of the National Academy of Sciences 99, (2002), 5133-5138.
Huang, et al., Langmuir 28, (2012), 665-665.
Hyman, A A, et al., "Beyond Oil and Water-Phase Transitions in Cells", Science 337, (2012), 1047-1049.
Kim, S H, et al., "Amphiphilic Crescent-Moon-Shaped Microparticles Formed by Selective Adsorption of Colloids", Journal of the American Chemical Society 133, (2011), 5516-5524.
Lingwood, D, et al., "Lipid Ralls as a Membrane-Organizing Principle", Science 327, (2010), 46-50.
Meyer, D E, et al., "Purification of recombinant proteins by fusion with thermally-responsive polypeptides", Nat Biotech 17, (1999), 1112-1115.
Nie, Z, et al., "Janus and Ternary Particles Generated by Microfluidic Synthesis", Design, Synthesis, and Self-Assembly. J Am Chem Soc 128, (2006), 9408-9412.
Strulson, C A, et al., "RNA catalysis through compartmentalization", Nat Chem 4, (2012), 941-946.
Utada, A. S., et al., "Monodisperse Double Emulsions Generated from a Microcapillary Device", Science, vol. 308, (Apr. 22, 2005), 537-541.
Wang, W, et al. "Hole-Shell Microparticles from Controllably Evolved Double Emulsions", Angewandte Chemie International Edition 52,, (2013), 8084-8087.
Simon, Joseph R., et al., "Programming molecular self-assembly of intrinsically disordered proteins containing sequences of low complexity", Nature Chemistry, vol. 9, (Jun. 2017), 509-515.
Simon, Joseph R., et al., "Programming molecular self-assembly of intrinsically disordered proteins containing sequences of low complexity", Nature Chemistry, Supplementary Information, (2017), 28 pgs.

* cited by examiner

Figure 1A Drop Formation

Colored Multicomponent Drops

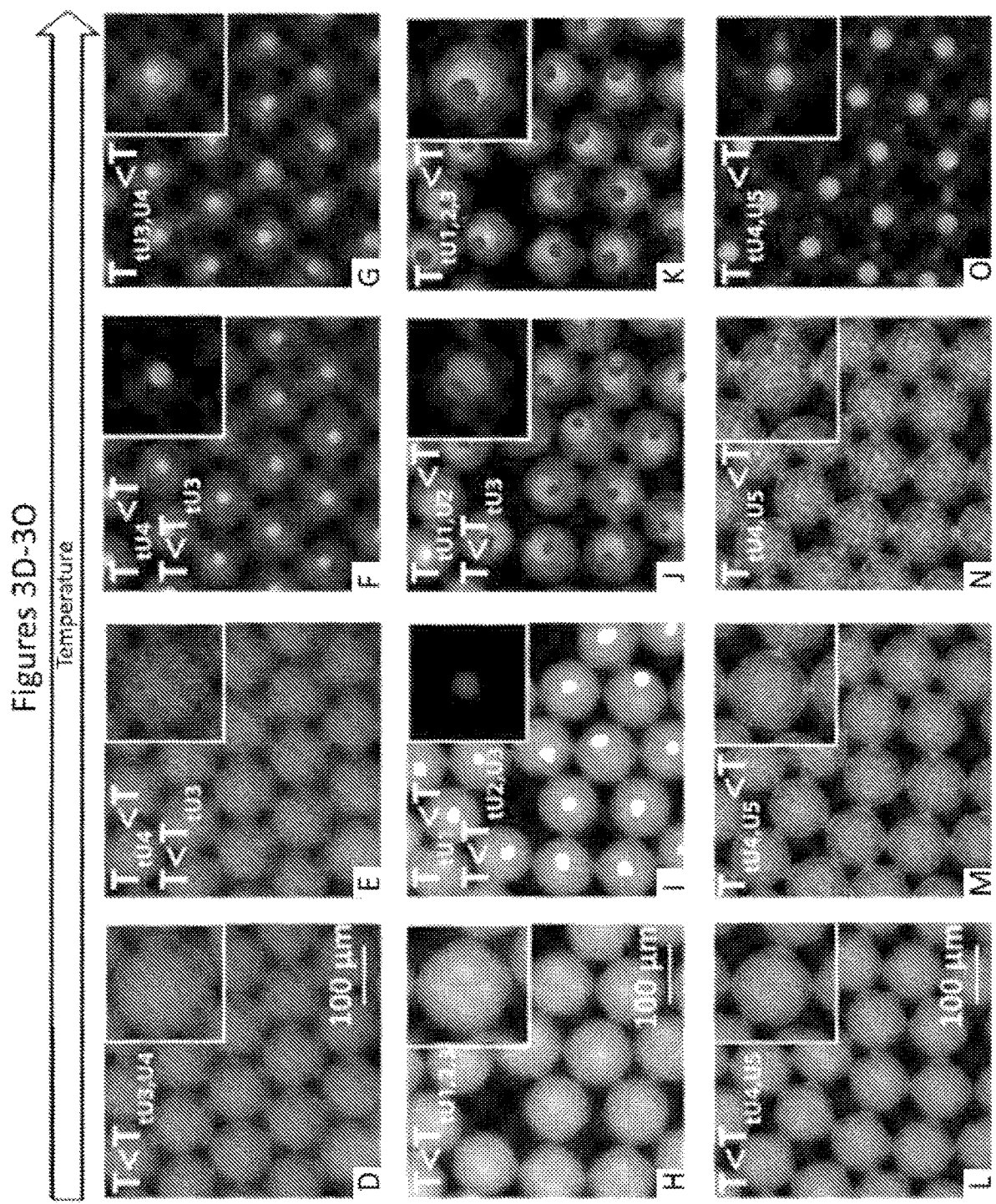

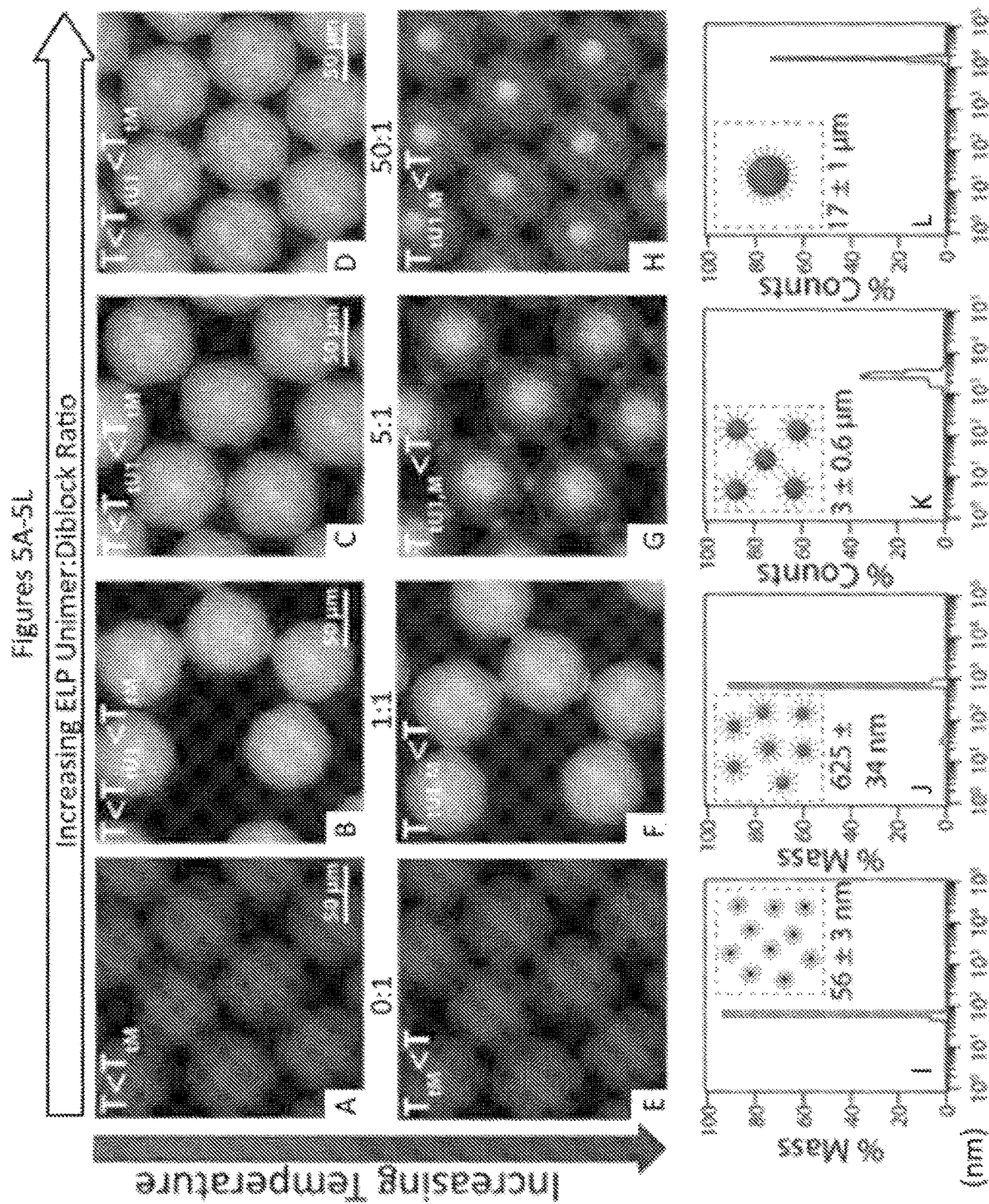

PROGRAMMABLE LIQUID, GEL AND BIOHYBRID COMPARTMENTS AND METHODS OF USE

CROSS REFERENCE TO RELATED APPLICATIONS

This application claims the benefit of PCT Patent Application No. PCT/US15/55836 filed Oct. 15, 2015, which claims the benefit of U.S. Provisional Application 62/064,057 filed Oct. 15, 2014, the disclosure of both of which is hereby incorporated by reference in its entirety.

FEDERAL FUNDING LEGEND

The invention was made with Government support under Federal Grant No. DMR-1121107 awarded by the National Science Foundation. The Government has certain rights in the invention.

TECHNICAL FIELD

The presently disclosed subject matter relates to programmable liquid, gel and biohybrid compartments and methods of use.

BACKGROUND

Multi-phase compartments are ubiquitous within biological cells, provide a powerful method for segregation of biomolecules, and are universal motifs in synthetic polymeric particle fabrication. Unfortunately, a broad platform for the in vitro programming of complex and hierarchical multi-phase structures has remained elusive. Techniques such as layer-by-layer deposition, molecular self-assembly, and microfluidic emulsion templating enable a high degree of control over the layering of distinct liquid or polymeric phases. However, these approaches have been limited to varying extents by: the need for complex and specialized fluidic devices, low fabrication throughput, limitations in achievable particle size, and constraints on material components due to assembly requirements. Thus, both current microfluidic and existing bulk techniques for fabrication of hierarchical liquid-liquid, gel and particle systems are severely lacking in scalability, size control, ease of fabrication, and morphological diversity.

SUMMARY OF THE DISCLOSURE

In some embodiments, the presently disclosed subject matter is directed to a method for making nano- to microscale liquid coacervate particles, the method comprising: stimulating a population of droplets including a solution of one or a mixture of components, wherein the stimulation induces a phase separation point of a first component; and maintaining stimulation at the phase separation point to form a coacervate domain of the first component within each of the droplets, wherein liquid coacervate particles are formed. In some embodiments, the population of droplets are formed using one or a combination of mechanical agitation, sonication, or microfluidics. In some embodiments, the population of droplets are aqueous droplets. In some embodiments, the population of droplets are aqueous droplets formed by sonication of the solution in oil or microfluidics of the solution in oil. In some embodiments, the population of aqueous droplets are in the form of a water-in-oil emulsion. In some embodiments, the liquid coacervate particles are reversibly formed by cessation of stimulation followed by re-stimulation and re-maintaining stimulation. In some embodiments, the first component includes a polymer. In some embodiments, the polymer includes a polypeptide. In some embodiments, the polypeptide includes at least a portion of an elastin-like polypeptide (ELP). In some embodiments, the method further comprises stabilizing the coacervate domain of the first component within each of the droplets to form capsule structures, wherein the coacervate domain of the first component remains consolidated upon cessation of stimulation at the phase separation point of the first component. In some embodiments, stabilizing includes formation of cross-links by one or a combination of covalent coordination, ionic interaction, disulfide bonds, or hydrogen bonds. In some embodiments, the phase separation point is a phase separation temperature and the stimulus includes heating. In some embodiments, the one or a mixture of components includes: a polymer, a synthetic polymer, a hydrophilic polymer, a hydrophobic polymer, an amphiphilic polymer, an amphiphilic diblock polymer, a protein, a nucleic acid, an epoxy, or a polysaccharide, and combinations thereof. In some embodiments, the stimulating includes: addition or removal of one or more of the components, evaporation of the droplets, controlled diffusion of one or more of the components, electrostatic quenching of one or more of the components, inducing a reaction of one or more of the components, isomerization of one or more of the components, crosslinking of one or more of the components, or crystallization of one or more of the components, and combinations thereof. In some embodiments, a substrate is immersed within the population of aqueous droplets in the form of a water-in-oil emulsion, and a tunable degree of the coacervate domain of the first component is formed on a surface of the substrate based on a wetting property of the substrate. In some embodiments, a grafted molecule is present on the surface of the substrate, and the degree of formation of the coacervate domain of the first component on the surface of the substrate is controlled by one or both of a level of interaction of the first component with the molecule and the wetting property of the substrate. In some embodiments, the method further comprises stabilizing the coacervate domain on the surface of the substrate by one or a combination of mineralization or formation of cross-links by one or a combination of covalent coordination, ionic interaction, disulfide bonds, or hydrogen bonds, wherein the coacervate domain remains consolidated upon cessation of stimulation at the phase separation point. In some embodiments, the substrate includes one or more of a medical device, a stent, a vascular graft, a catheter, a biosensor, a drug reservoir, or a cell culture substrate. In some embodiments, the population of droplets are aqueous and the solution further includes one or a combination of a cell, a virus, or a nanoparticle having a coating of at least one component to cause recruitment of the coated cell, virus, or nanoparticle to the coacervate domain of the respective component within each of the droplets. In some embodiments, the first component has an attached bioactive agent, wherein the bioactive agent includes one or a combination of: a drug, a protein, a peptide, a peptide hormone, a ligand, a cell-signaling ligand, or an RGD cell binding domain, to cause recruitment of the drug, protein, peptide, peptide hormone, ligand, cell-signaling ligand, or RGD cell binding domain to the coacervate domain of the first component within each of the droplets. In some embodiments, the first component is a polypeptide and the bioactive agent is attached through an amino acid linkage or through a chemical linkage through a reactive peptide residue. In some embodiments, the polypeptide attached to the bioactive agent includes a protease cleavage site. In some embodiments, the solution includes one or more additional components each having an additional phase separation point, the method further comprising: stimulating the population of aqueous droplets, wherein stimulation induces a phase separation point of the additional component; maintaining stimulation at the additional phase separation point to form a coacervate domain of the additional component within each of the droplets; and optionally repeating the stimulating and maintaining for one or more additional components. In some embodiments, the first component and the additional components include polymers. In some embodiments, the polymers include polypeptides. In some embodiments, the polypeptides include at least a portion of an elastin-like polypeptide (ELP). In some embodiments, the first component and the additional component(s) have similar phase separation points and a blended alloy coacervate domain is formed. In some embodiments, the coacervate domain of the first component and the coacervate domain(s) of the additional component(s) form a multilayered coacervate domain, a blended alloy coacervate domain, or a combination thereof. In some embodiments, the first phase separation point and the additional phase separation point(s) are each a phase separation temperature, and the stimulus includes heating. In some embodiments, the solution includes at least the first component and a surfactant for controlling a size of the coacervate domain. In some embodiments, the surfactant includes an amphiphilic diblock polymer. In some embodiments, the first component is a hydrophobic ELP polymer and the amphiphilic diblock polymer is an ELP diblock polymer. In some embodiments, a ratio of the hydrophobic ELP polymer to the amphiphilic ELP diblock polymer ranges from about 1:1 to about 50:1, and the size of an outermost coacervate domain ranges from about 50 nm to about 20 µm. In some embodiments, the method further comprises stabilizing at least an outermost coacervate domain within each of the droplets to form capsule structures, wherein the outermost coacervate domain remains consolidated upon cessation of stimulation at the phase separation point for the outermost coacervate domain. In some embodiments, stabilizing includes formation of cross-links by one or a combination of covalent coordination, ionic interaction, disulfide bonds, or hydrogen bonds. In some embodiments, a substrate is immersed within the population of aqueous droplets in the form a water-in-oil emulsion, and a tunable degree of the coacervate of the first component and the additional component(s) is formed on a surface of the substrate based on a wetting property of the substrate. In some embodiments, a molecule is grafted on the surface of the substrate, and the degree of formation of the coacervate domain of the first component and the additional component(s) on the surface of the substrate is controlled by one or both a level of interaction of one or both of the first component and the additional component(s) with the molecule and the wetting property of the substrate. In some embodiments, the coacervate domain of the first component and the additional component(s) on the surface of the substrate is in the form of a single layer coacervate domain, a multilayered coacervate domain, a blended alloy coacervate domain, or combinations thereof. In some embodiments, the method further comprises stabilizing at least an outermost coacervate domain on the surface of the substrate by one or a combination of mineralization or formation of cross-links by one or a combination of covalent coordination, ionic interaction, disulfide bonds, or hydrogen bonds, wherein the outermost coacervate domain remains consolidated upon cessation of stimulation at the phase separation point for the outermost coacervate domain. In some embodiments, the substrate includes one or more of a medical device, a stent, a vascular graft, a catheter, a biosensor, a drug reservoir or a cell culture substrate. In some embodiments, the population of droplets are aqueous and the solution further includes one or a combination of a cell, a virus, or a nanoparticle having a coating of at least one component to cause recruitment of the coated cell, virus, or nanoparticle to the coacervate domain of the respective component within each of the droplets. In some embodiments, one or more of the components has an attached bioactive agent, wherein the bioactive agent includes one or a combination of: a drug, a protein, a peptide, a peptide hormone, a ligand, a cell-signaling ligand, or an RGD cell binding domain, to cause recruitment of the drug, protein, peptide, peptide hormone, ligand, cell-signaling ligand, or RGD cell binding domain to the coacervate domain of the component within each of the droplets. In some embodiments, at least two components have the attached bioactive agent. In some embodiments, the one or more components is a polypeptide and the bioactive agent is attached through an amino acid linkage or through a chemical linkage through a reactive peptide residue. In some embodiments, the one or more polypeptides attached to the bioactive agent includes a protease cleavage site.

In some embodiments, the presently disclosed subject matter is directed to a method for coating a substrate, the method comprising: stimulating a solution of one or a mixture of components, wherein a substrate is immersed within the solution, wherein the stimulation induces a phase separation point of a first component; maintaining stimulation at the phase separation point to form a degree of a coacervate domain of the first component on a surface of the substrate based on a wetting property of the substrate; and repeating the stimulating and maintaining for one or more additional components in the mixture to form a coacervate domain of the additional component. In some embodiments, the solution is aqueous. In some embodiments, the first component and the additional component(s) include polymers. In some embodiments, the polymers include polypeptides. In some embodiments, the polypeptides include at least a portion of an elastin-like polypeptide (ELP). In some embodiments, the first component and the additional component(s) have similar phase separation points and a blended alloy coacervate domain is formed on the surface of the substrate. In some embodiments, the coacervate domain of the first component and the coacervate domain(s) of the additional component(s) on the surface of the substrate is in the form of a single layer coacervate domain, a multilayered coacervate domain, a blended alloy coacervate domain, or combinations thereof. In some embodiments, a molecule is grafted on the surface of the substrate, and the degree of formation of the coacervate domain of the first component and the additional component(s) on the surface of the substrate is controlled by one or both a level of interaction of one or both of the first component and the additional component(s) with the molecule and the wetting property of the substrate. In some embodiments, the method further comprises stabilizing at least an outermost coacervate domain on the surface of the substrate by one or a combination of mineralization or formation of cross-links by one or a combination of covalent coordination, ionic interaction, disulfide bonds, or hydrogen bonds, wherein the outermost coacervate domain remains consolidated upon cessation of stimulation at the phase separation point for the outermost coacervate domain. In some embodiments, the substrate includes one or more of a medical device, a stent, a vascular graft, a catheter, a biosensor, a drug reservoir, or a cell culture substrate. In some embodiments, the solution further includes one or a combination of a cell, a virus, or a nanoparticle, and wherein the cell, virus, or nanoparticle includes a coating of at least one of the components to cause recruitment of the cell, virus, or nanoparticle to the coacervate domain of the respective component. In some embodiments, one or more of the components has an attached bioactive agent, wherein the bioactive agent includes one or a combination of: a drug, a protein, a peptide, a peptide hormone, a ligand, a cell-signaling ligand, or an RGD cell binding domain, to cause recruitment of the drug, protein, peptide, peptide hormone, ligand, cell-signaling ligand, or RGD cell binding domain to the coacervate domain of the respective component. In some embodiments, at least two of the components have the attached bioactive agent. In some embodiments, the one or more components is a polypeptide and the bioactive agent is attached through an amino acid linkage or through a chemical linkage through a reactive peptide residue. In some embodiments, the one or more polypeptides attached to the bioactive agent includes a protease cleavage site. In some embodiments, the first phase separation point and the additional phase separation point(s) are each a phase separation temperature, and the stimulus includes heating. In some embodiments, the one or a mixture of components includes: a polymer, a synthetic polymer, a hydrophilic polymer, a hydrophobic polymer, an amphiphilic polymer, an amphiphilic diblock polymer, a protein, a nucleic acid, an epoxy, or a polysaccharide, and combinations thereof. In some embodiments, the stimulating includes: addition or removal of one or more of the components, evaporation of the solution, controlled diffusion of one or more of the components, electrostatic quenching of one or more of the components, inducing a reaction of one or more of the components, crosslinking of one or more of the components, isomerization of one or more of the components, or crystallization of one or more of the components, and combinations thereof.

In some embodiments, the presently disclosed subject matter is directed to a coated substrate produced by a process comprising: stimulating a solution of one or a mixture of components, wherein a substrate is immersed within the solution, wherein the stimulation induces a phase separation point of a first component; maintaining stimulation at the phase separation point to form a degree of a coacervate domain of the first component on a surface of the substrate based on a wetting property of the substrate; and repeating the stimulating and maintaining for one or more additional components in the mixture to form a coacervate domain of the additional component. In some embodiments, the process further comprises stabilizing at least an outermost coacervate domain on the surface of the substrate by one or a combination of mineralization or formation of cross-links by one or a combination of covalent coordination, ionic interaction, disulfide bonds, or hydrogen bonds, wherein the outermost coacervate domain remains consolidated upon cessation of stimulation at the phase separation point for the outermost coacervate domain. In some embodiments, the substrate includes one or more of a medical device, a stent, a vascular graft, a catheter, a drug reservoir or a cell culture substrate.

In some embodiments, the presently disclosed subject matter is directed to a coated substrate produced by a process comprising: stimulating a population of aqueous droplets in the form of a water-in-oil emulsion, wherein the droplets include a solution of one or a mixture of components, wherein a substrate is immersed within the population of aqueous droplets, and wherein the stimulation induces a phase separation point of a first component; maintaining stimulation at the phase separation point to form a tunable degree of a coacervate domain of the first component on a surface of the substrate based on a wetting property of the substrate; and repeating the stimulating and maintaining for one or more additional components in the mixture to form a coacervate domain of the additional component. In some embodiments, the process further comprises stabilizing at least an outermost coacervate domain on the surface of the substrate by one or a combination of mineralization or formation of cross-links by one or a combination of covalent coordination, ionic interaction, disulfide bonds, or hydrogen bonds, wherein the outermost coacervate domain remains consolidated upon cessation of stimulation at the phase separation point for the outermost coacervate domain. In some embodiments, the substrate includes one or more of a medical device, a stent, a vascular graft, a catheter, a drug reservoir, a biosensor, or a cell culture substrate.

In some embodiments, the presently disclosed subject matter is directed to a nano- to microscale liquid coacervate particle composition produced by a process comprising: stimulating a population of droplets including a solution of one or a mixture of components, wherein the stimulation induces a phase separation point of a first component; maintaining stimulation at the phase separation point to form a coacervate domain of the first component within each of the droplets, wherein liquid coacervate particles are formed; and optionally repeating the stimulating and maintaining for the one or more additional components in the mixture to form a coacervate domain of the additional component within each of the droplets. In some embodiments, the process further comprises stabilizing at least an outermost coacervate domain within each of the droplets to form capsule structures, wherein the outermost coacervate domain remains consolidated upon cessation of stimulation at the phase separation point for the outermost coacervate domain. In some embodiments, stabilizing includes formation of cross-links by one or a combination of covalent coordination, ionic interaction, disulfide bonds, or hydrogen bonds. In some embodiments, the first component and the additional components include polymers. In some embodiments, the polymers include polypeptides. In some embodiments, the polypeptides include at least a portion of an elastin-like polypeptide (ELP). In some embodiments, the first component and the additional component(s) have similar phase separation points and a blended alloy coacervate domain is formed. In some embodiments, the coacervate domain of the first component and the coacervate domain(s) of the additional component(s) form a multilayered coacervate domain, a blended alloy coacervate domain, or a combination thereof. In some embodiments, the first phase separation point and the additional phase separation point(s) are each a phase separation temperature, and the stimulus includes heating. In some embodiments, the population of droplets are aqueous droplets. In some embodiments, the solution includes at least the first component and a surfactant for controlling a size of the coacervate domain. In some embodiments, the population of droplets are aqueous droplets and the surfactant includes an amphiphilic diblock polymer. In some embodiments, the first component is a hydrophobic ELP polymer and the amphiphilic diblock polymer is an ELP diblock polymer. In some embodiments, a ratio of the hydrophobic ELP polymer to the amphiphilic ELP diblock polymer ranges from about 1:1 to about 50:1, and a size of an outermost coacervate domain ranges from about 50 nm to about 20 μm. In some embodiments, the population of droplets are aqueous and the solution further includes one or a combination of a cell, a virus, or a nanoparticle having a coating of at least one component to cause recruitment of the coated cell, virus, or nanoparticle to the coacervate domain of the respective component within each of the droplets. In some embodiments, one or more of the components has an attached bioactive agent, wherein the bioactive agent includes one or a combination of: a drug, a protein, a peptide, a peptide hormone, a ligand, a cell-signaling ligand, or an RGD cell binding domain, to cause recruitment of the drug, protein, peptide, peptide hormone, ligand, cell-signaling ligand, or RGD cell binding domain to the coacervate domain of the respective component within each of the droplets. In some embodiments, at least two components have the attached bioactive agent. In some embodiments, the one or more components is a polypeptide and the bioactive agent is attached through an amino acid linkage or through a chemical linkage through a reactive peptide residue. In some embodiments, the one or more polypeptides attached to the bioactive agent includes a protease cleavage site.

BRIEF DESCRIPTION OF THE DRAWINGS

The foregoing aspects and other features of the disclosure are explained in the following description, taken in connection with the accompanying drawings, wherein:

FIG. 1A depicts droplets containing multiple fluorescently labeled components according to at least one embodiment of the present disclosure;

DETAILED DESCRIPTION OF THE DISCLOSURE

Figures 1B, 1C:
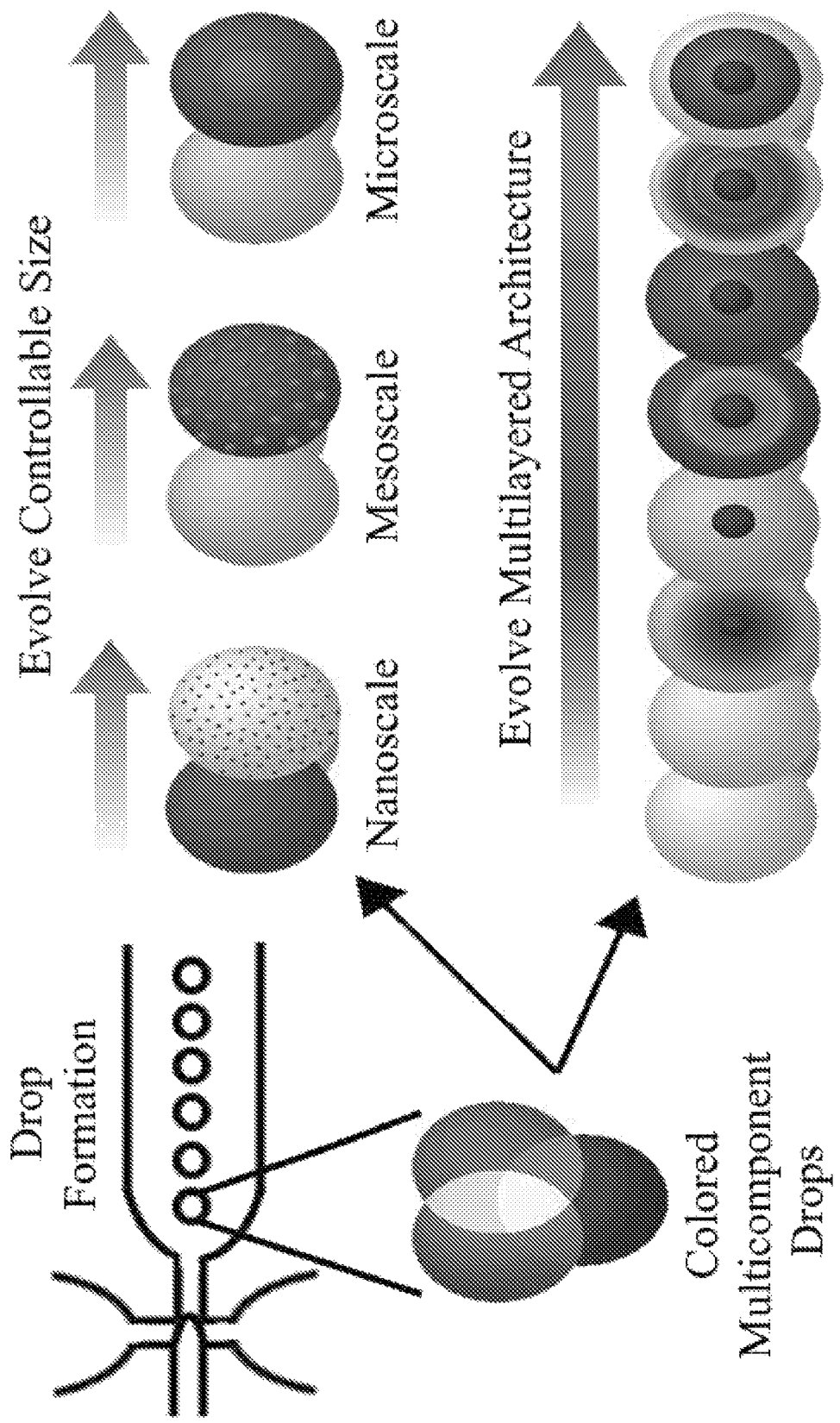
FIG. 1B depicts a schematic representing mixtures of up to three components in a solution according to at least one embodiment of the present disclosure.
FIG. 1C depicts nanoscale, mesoscale and microscale coacervate domains evolved from droplets containing mixtures of components according to at least one embodiment of the present disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The presently disclosed invention provides the ability to program the self-assembly of hierarchical liquid compartments comprised of polymers from solutions and suspensions by encoding polymer phase transition behavior and surface interactions at the building block level. The ability to encode information needed for programmable self-assembly into complex patterns is a hallmark of biological materials and emulating these features allows for the formation of a variety of practically useful materials. The inventions of the present disclosure advantageously affords the diversity to program phase separation events in liquid structures spanning the nano- to micro-scale. The present disclosure is valid for both synthetic and biological materials. The inventions are demonstrated in the examples infra, which include stimulus-induced self-assembly of phase-transitioned aqueous architectures comprised of disordered proteins engineered via recombinant genetics. The inventions disclosed herein enable exquisite control of polymeric building blocks through the tailoring of structure, molecular weight and composition at the individual amino acid (monomer) level. The self-assembled nano, meso, micro and macro structures may further find utility in drug delivery, bioanalytical systems, controlled cell culture, tissue engineering, biomanufacturing and drug discovery.

The presently disclosed invention provides the ability to program the self-assembly of hierarchical liquid coacervate particles. In one embodiment a method is provided for making nano- to microscale liquid coacervate particles. The method includes stimulating a population of droplets having a solution of one or a mixture of components to induce a phase separation point of a first component. By maintaining stimulation at the phase separation point, a coacervate domain of the first component within each of the droplets can be formed. Liquid coacervate particles are formed through maintaining stimulation of the droplet containing one component or a mixture of components.

The solution can include one or more additional components each having an additional phase separation point. The method can include further stimulating of the population of aqueous droplets to induce a phase separation point of the additional components and maintaining stimulation at the additional phase separation point to form a coacervate domain of the additional component within each of the droplets. Optionally, repeating the stimulating and the maintaining for one or more additional components can be performed to form additional coacervate domains within the droplets. Examples of the liquid coacervate particles of the invention are shown in FIGS. 1-6.

The formation of multiple all-aqueous protein-rich compartments with distinct boundaries was directed by programming the phase behavior of thermally-responsive elastin-like polypeptide (ELP) components (FIG. 1B) within the confinement of water microdroplets (FIG. 1A). This approach enables reversibly fabrication of (1) single- and multi-modal population protein compartments spanning the nano-, meso-, and micro-scale and (2) multilayered micro-architectures (FIG. 1C) by controlling phase behavior via simple modification of the ELP components. FIG. 1A depicts droplets containing multiple fluorescently labeled ELP polymers. FIG. 1B depicts a schematic representing mixtures of up to three polymers in a solution. FIG. 1C depicts nanoscale, mesoscale and microscale particles in the top portion, and multilayered microscale particles in the bottom portion, evolved from homogeneous droplets containing mixtures of ELP polymers by controlled phase separation and wetting.

ELPs are a class of disordered, stimuli responsive protein polymers based on the repetitive elastin-based motif Val-Pro-Gly-Xaa-Gly (SEQ ID NO: 1), where Xaa is a tailorable guest residue. The hallmark characteristic of these polymers is their lower critical solution temperature (LCST) phase transition behavior, where above the cloud point transition temperature ($T_t$) they phase separate to form polymer rich coacervate domains. For this demonstration, the strategy centers on heating through the solution coexistence boundary into the unstable region of the miscibility gap to direct phase transition via spinodal decomposition; here, spontaneous amplification of concentration fluctuations results in rapid formation and coarsening of protein-rich domains that are separated from a water-rich phase (FIG. 2).

Figure 2:
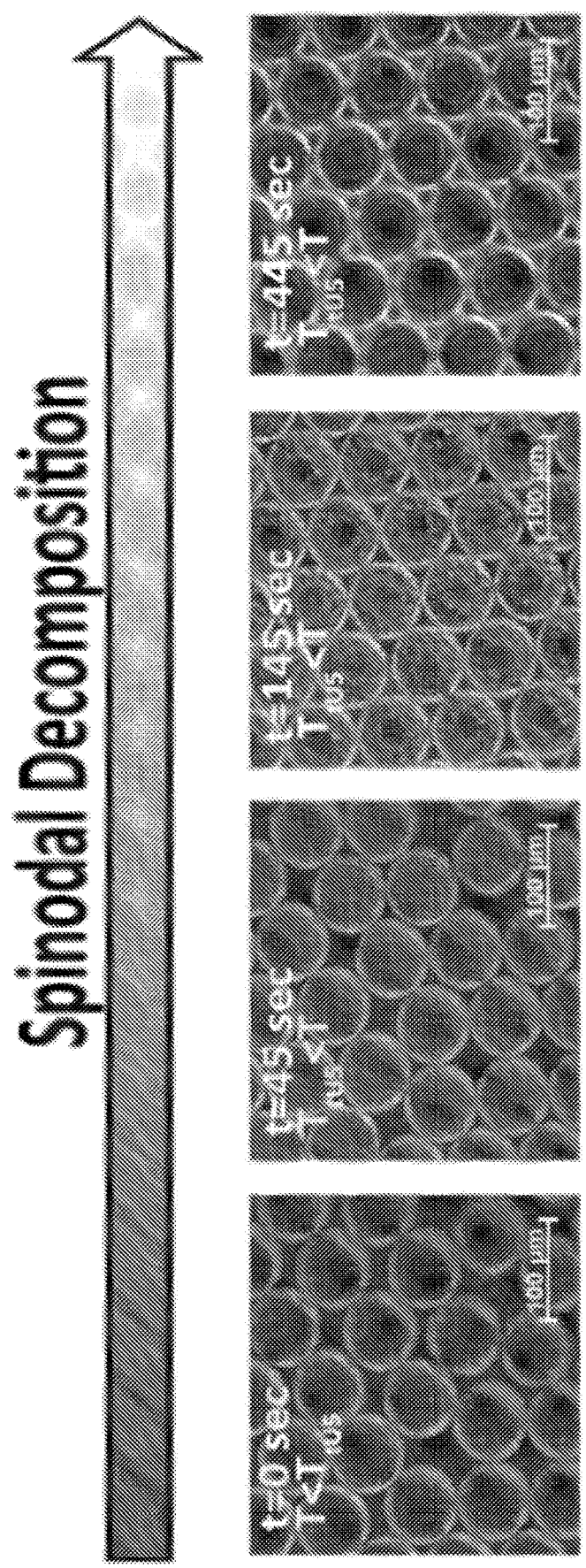
FIG. 2 depicts time-lapse darkfield microscope images of thermally-induced spinodal decomposition of polymer within droplets according to at least one embodiment of the present disclosure.

FIG. 2 depicts time-lapse darkfield microscope images of thermally-induced spinodal decomposition of polymer within water drops. Phase separated microdomains coarsen with time to form a liquid-liquid structure comprised of a polymer-rich coacervate (dark spherical center) surrounded by a water-rich layer. Within the confinement of microdroplets, spinodal decomposition provides a powerful approach for building compartmentalized liquid-liquid structures through the modulation of polymeric component phase behavior. It should be noted that other viable phase separation mechanisms include: nucleation and growth (metastable region); multi-component mixing-driven phase separation via component addition or removal, solvent evaporation, and/or controlled diffusion; electrostatic quenching; reaction-induced; crosslinking; and crystallization.

In one embodiment, a nano- to microscale liquid coacervate particle composition is provided that is produced by a process including stimulating a population of droplets including a solution of one or a mixture of components, wherein the stimulation induces a phase separation point of a first component and maintaining stimulation at the phase separation point to form a coacervate domain of the first component within each of the droplets. In this manner liquid coacervate particles are formed. Optionally, the method includes repeating the stimulating and maintaining for the one or more additional components in the mixture to form a coacervate domain of the additional component within each of the droplets.

The population of droplets can be formed using one or a combination of mechanical agitation, sonication, or microfluidics. The population of droplets can be formed by sonication of a solution in oil or microfluidics of a solution in oil. The population of droplets can be aqueous. The aqueous droplets can be in the form of a water-in-oil emulsion.

The liquid coacervate particles can be reversibly formed by cessation of stimulation followed by re-stimulation and re-maintaining the stimulation. Such methods can be useful as bioreactors or for temporarily sequestering reactants.

Figure 3A:
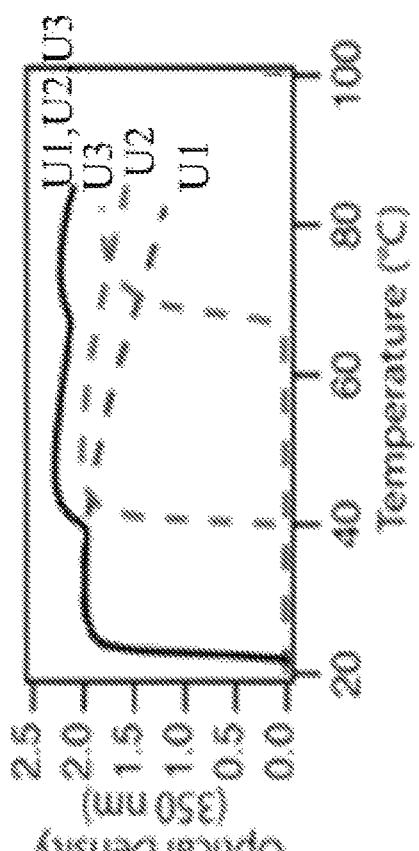
FIGS. 3A-3O depict spinodal decomposition of multiple ELP components for formation of blended and multilayered microparticles according to at least one embodiment of the present disclosure.
Figure 3B:
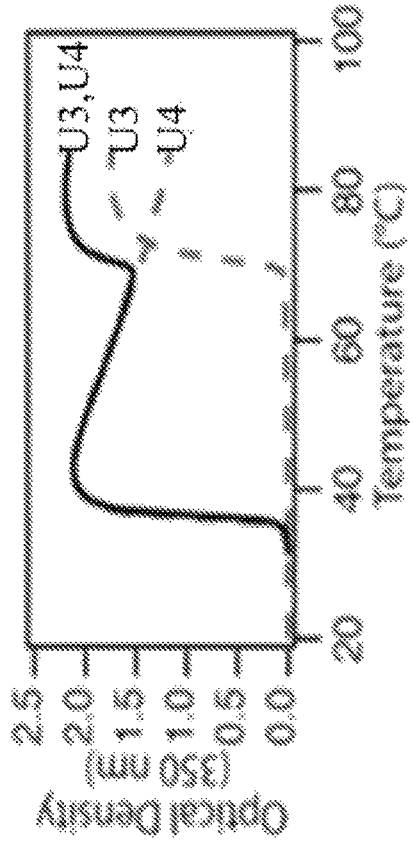
Figure 3C:
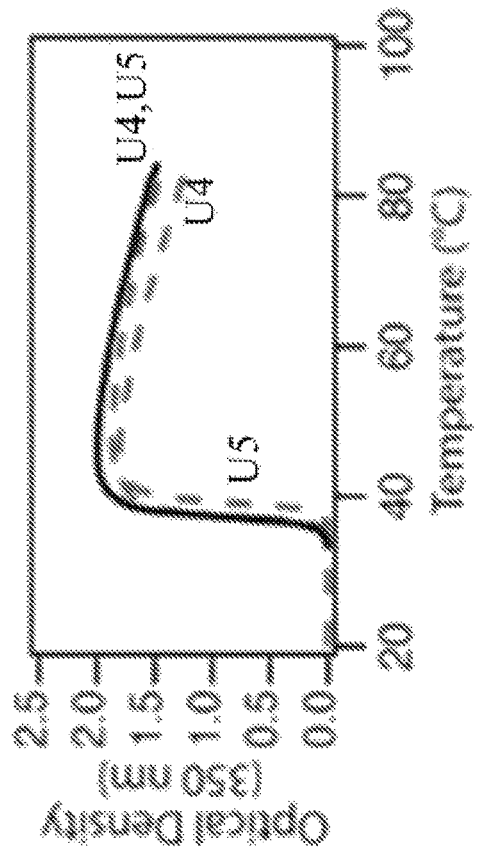

The programming of hierarchical aqueous polymeric layers immiscible not only with the surrounding water solvent, but also orthogonal to other co-existing polymeric phases is demonstrated. The results reveal the phase tunability of polymer mixtures through simple tailoring of the monomer (amino acid) sequence and molecular weight. Five different homopolymers (labeled U1 through U5) were used, each with distinct phase diagrams. FIGS. 3A-3F depict spinodal decomposition of multiple ELP components for formation of blended and multilayered microparticles. FIGS. 3A-3C depicts temperature-controlled spectrophotometry of bulk ELP solutions. The bulk phase transition temperatures of various homopolymer mixtures are characterized using spectrophotometry (FIGS. 3A-3C). A mixture of U3 and U4 shows two independent spinodal decomposition events, as depicted in FIG. 3A. A mixture of U1, U2, and U3 shows three independent spinodal decomposition events, as depicted in FIG. 3B. A mixture of U2 and U5 shows a single spinodal decomposition event, as depicted in FIG. 3C.

When the cloud point temperatures of different components within a homopolymer mixture are sufficiently separated from one another, observe multiple phase separation events were observed (FIGS. 3A and 3B, solid curves) that correspond to the phase separation events of their respective individual components (dashed curves). Conversely, simultaneous phase separation (FIG. 3C, solid curve) of two ELP homopolymers were observed in a mixture if the transition temperature of their individual components is similar (dashed curves). By carefully traversing these multicomponent phase diagrams it was possible to controllably form either (1) multilayered or (2) blended 'alloy' coacervates via discretized heating and selectively inducing various phase separation events as predetermined in bulk.

FIGS. 3D-3O depict fluorescent microscope images of hierarchically structured microparticles. Double-layered coacervates made of U4 (lightest coacervate in far-right image) and U3 (larger coacervate encapsulating U4 in far-right image) are depicted in FIGS. 3D-3G. Triple-layered coacervates made of U1 (light coacervate of middle-left image), U2 (coacervate of middle-right image encapsulating U1), and U3 (coacervate of far-right image encapsulating U2) are depicted in FIGS. 3H-3K. Alloy coacervates made of U2 and U5 are depicted in FIGS. 3L-3O. The inset images of FIGS. 3D-3O depict fluorescent channel(s) of ELPs that have and/or are phase separating. The double-layer (FIGS. 3D-3G) and triple-layer (FIGS. 3H-3K) protein coacervates were assembled by exploiting the effects of micro-confinement on the phase separation process. By encapsulating mixtures of homopolymers inside droplets and subsequently heating in a step-wise fashion, the unstable region of the phase diagram for each successive increasingly hydrophilic protein component was targeted; the system is held above each transition temperature until phase separation of the target protein proceeds to completion. Subsequent phase separation events in this manner result in the formation of n coacervate layers, where n is the number of polymeric components inside the droplets with dissimilar phase diagrams. Only one polymer type populates each phase-transitioned layer.

The formation of wetting architectures is described by component interfacial tensions ($\gamma_{i/j}$) and the spreading parameter (S):

$$S = \gamma_{IP/Water} - (\gamma_{IP/MP} + \gamma_{MP/Water}).$$

A positive spreading parameter (S>0) results in the formation of wetting layers, which is due to a high degree (≥80% by composition) of chemical homology between the protein polymers. By contrast, a negative spreading parameter (S<0) will result in Janus structures. Thus, interfacial energies and the accompanying spreading behavior are a key module for structural design with the method presented herein.

In contrast to distinct layered liquid phases, protein coacervate 'alloy' blends were formed when the phase transition is initiated for a binary mixture comprised of two different polymers with different chemical composition but with similar phase transition temperatures, as evidenced by inspection of FIGS. 3L-3O. Thus, both physical and chemical properties can be engineered into each liquid phase layer by tailoring the system phase behavior at the building block level.

Figure 4:
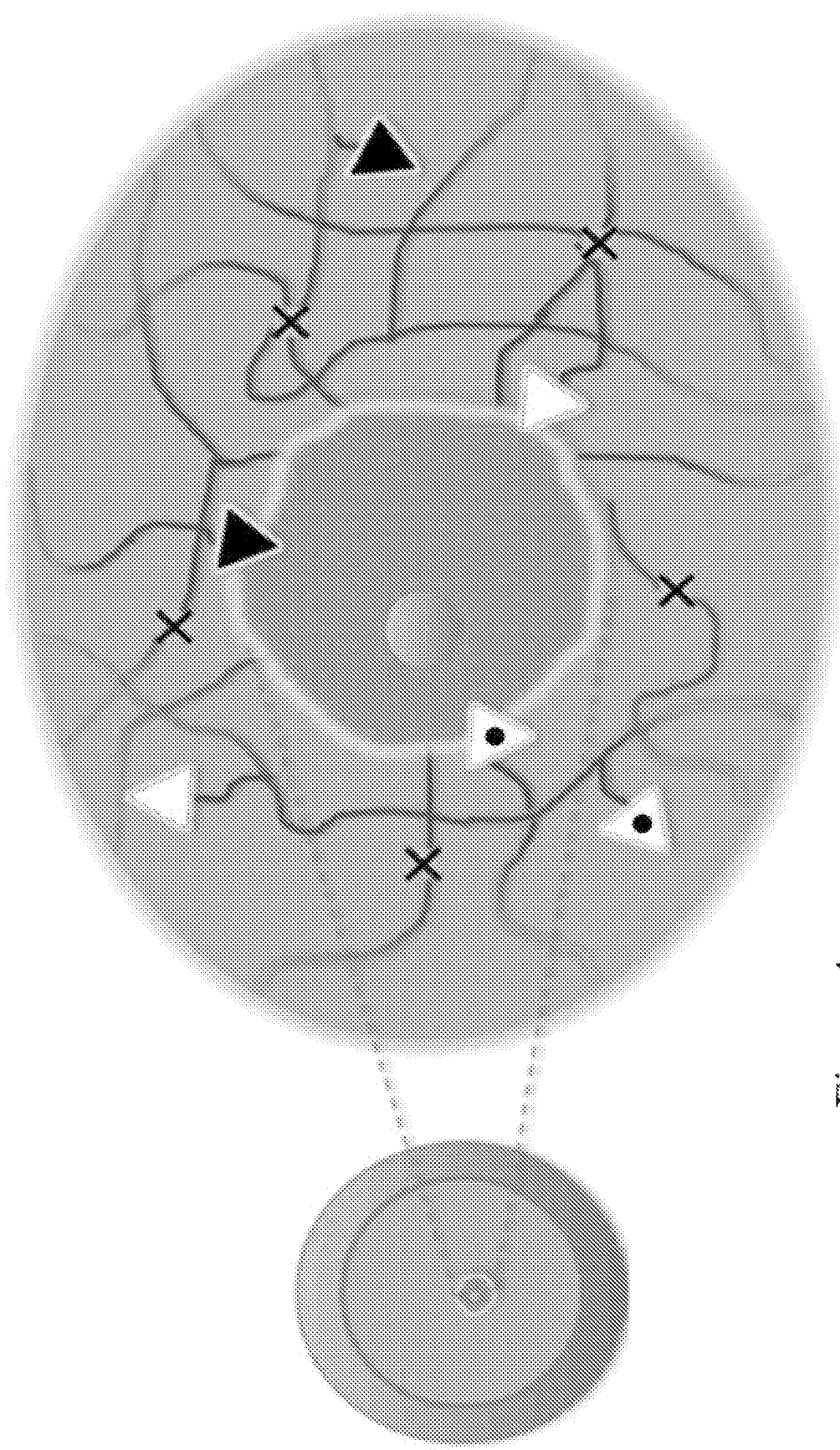
FIG. 4 depicts the formation of multi-liquid phase coacervate domains and functionalized biomaterials according to at least one embodiment of the present disclosure.

The types and spatiotemporal distributions of signaling molecules detected by target cells in extracellular regulation are the subject of extensive investigations. Thus, there is a growing need for creating diverse extracellular matrices (ECMs) from an array of programmable biologically functional building blocks, with versatile modular design. The method of manipulating polymer assembly can allow (i) high-throughput encapsulation of cells, cellular components (e.g., organelles) or viruses within biocompatible (e.g., polypeptide) gel microarrays, (ii) capturing cells, cellular components (e.g., organelles) or viruses within tailorable layers of single population or 'alloy' blends of gels, each with distinct intrinsic physicochemical functionalization, (iii) capturing cells, cellular components (e.g., organelles) or viruses within capsule-like structures with modular core and shell properties, (iv) spatial organization of immobilized cell-signaling ligands and within the gel matrix, (v) tailoring of gel ECM mechanical properties, (vi) integration of degradable (e.g., protease-cleavable) linkages, and (vii) combinations thereof (shown schematically in FIG. 4). In FIG. 4, the dotted triangle represents integrin ligands (recreate cell-cell and cell-ECM interactions), the black triangle represents immobilized soluble biomolecules (growth factors, cytokines), the white triangle represents recapitulated cell-cell interactions (ephrins, cadherins, CAMs), and X represents protease sensitive degradation sites. The flexibility of these methods can be taken advantage of for forming multi-liquid phase compartments to create functionalized biomaterials for ECM assembly that have potential for direct translation to regenerative medicine, cell-culture, cell-based therapies, drug discovery, drug delivery, and tissue engineering related markets.

Figure 5M:
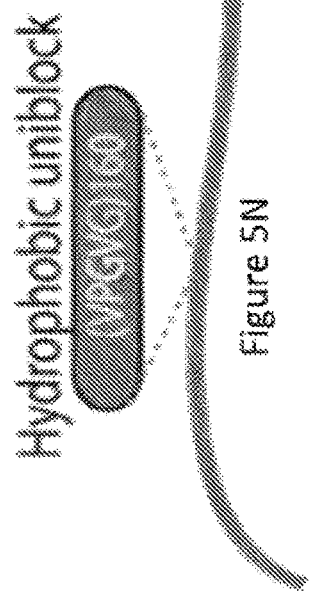
FIGS. 5A-5P depicts nano-, meso- and microparticles formed by arrested coarsening according to at least one embodiment of the present disclosure.
Figure 5O:
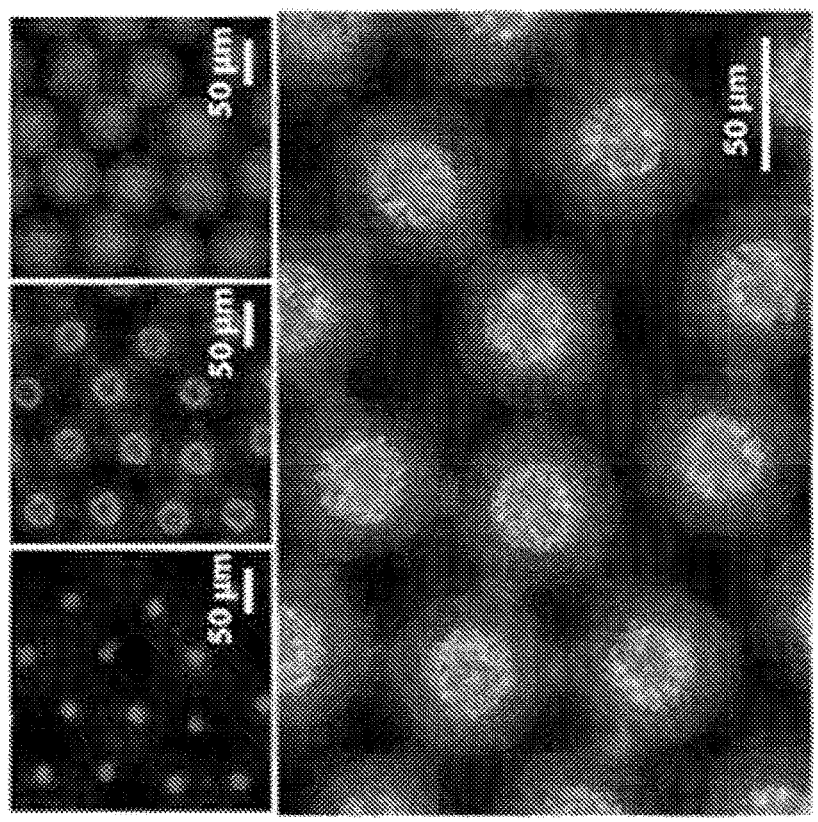
Figure 5N:
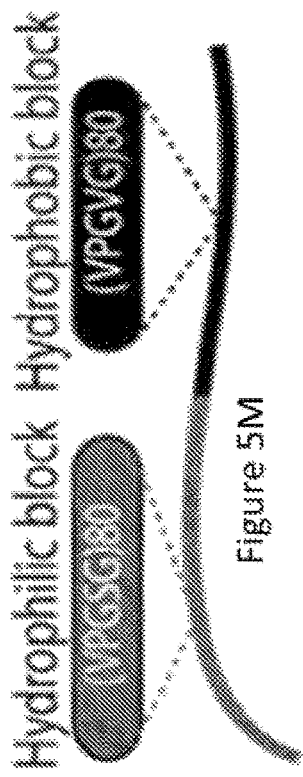
Figure 5P:
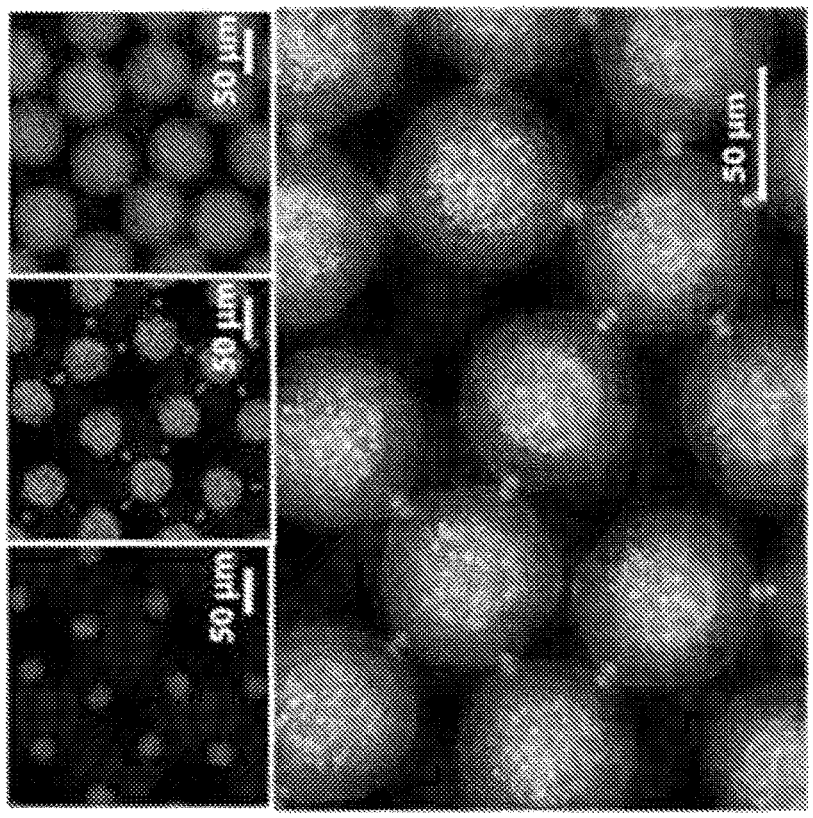

The specific characteristics of phase transitioned liquid-liquid phases depend strongly on molecular and surface interactions. Validating this was possible by utilizing protein diblock surfactants (called D1) to self-assemble populations of uniform polymer-rich compartments with controllable size. FIGS. 5A-5P depict nano-, meso- and microparticles formed by arrested coarsening. FIGS. 5M-5N depicts a schematic showing sequences of the ELP diblock (FIG. 5M) and U1 uniblock (FIG. 5N). The ELP diblocks consist of two adjoined blocks of dissimilar amino acid repeats. The amphiphilic nature of these diblock polypeptides enables the temperature-triggered self-assembly of nanoscale micelles (D≈56 nm) when D1 is the lone component. FIGS. 5A-5D depicts fluorescent microscope images of water drops containing various ratios of darker-labeled ELP diblock and lighter-labeled U1. The diblock arrests coarsening of phase-separated U1 uniblock domains by acting as a surface-stabilizing agent. In the case of a homopolymer/diblock mixture, phase-separated polypeptide compartments that span the nano-, meso-, and micro-scale (FIGS. 5M-5N) were fabricated by simply modulating the stoichiometric ratio of the components. Upon heating the mixture into the unstable region of the homopolymer phase diagram, the homopolymer begins to phase separate via spinodal decomposition. Coarsening of the polymeric-rich liquid domains is arrested at a specific size by the stabilizing protein amphiphiles; the protein compartment size is a function of diblock quantity. This strategy provides access to the generally less-accessible meso-scale and offers a mechanism for the fabrication of particles spanning multiple length scales via programmed phase separation.

The resultant protein compartments have a narrow size distribution (FIGS. 5I-5L), presumably due to mass conservation and molecular packing. FIGS. 5I-5L depict a schematic of the polypeptide compartments formed by varying U1/diblock ratios. The diameters of the resultant protein phase puncta are: (U1 to diblock ratio in parentheses): 56±3 nm (0:1), 625±34 nm (1:1), 3±0.6 m (5:1), and 17±1 m (50:1). Furthermore, these phase-transitioned domains do not experience appreciable precipitation and are kinetically stable for up to 24 hours.

Biomaterial can be fabricated by covalently crosslinking the coarsen-arrested protein microcompartments. Multi-modal populations of protein-rich water compartments can be fabricated by supplementing the aqueous precursor solution with a second population of U2 homopolymer.

By simply changing the stoichiometric ratios of mixtures U1, U2, and D1 two distinct, orthogonally phase-separated populations of similar-sized microcompartments were created (FIG. 5O) and a single coacervate compartment coexisting with numerous smaller compartments (FIG. 5P); this type of multi-component protein compartmentalization can be useful for recreating complex non-membrane bound intracellular microenvironments through controlled segregation of biomacromolecules. FIGS. 5O-5P depict fluorescent microscope images of distinct uniblock polypeptide domains. FIG. 5O consists of a bimodal population of U1 (top-left inset) and U2 (top-middle inset) microcompartments with ratio of total uniblock to diblock (top-right inset) of 5:1. FIG. 5P depicts fully coarsened U1 coacervate (top-left inset) surrounded by U2 microcompartments (top-middle inset) with ratio of total uniblock to diblock (top-right inset) of 50:1. Top panels of FIGS. 5O and 5P show U1 (left), U2 (middle) and D1 (right) fluorescent channels; bottom panels of FIGS. 5O and 5P are overlay images.

This technology can enable one-pot fabrication of complex hierarchical biological and synthetic particle architectures through preprogrammed phase separation and self-assembly. The ability to evolve complex structures is in contrast to microfluidic or layer-by-layer methods, where each layer or phase is added in sequential steps; thus, massive scale up in production, size control, and reduced fabrication costs is facilitated by the technology. Additionally, phase separated low-surface energy water compartments, crowded with biomolecules, mimics non-membrane bound organelles within the cytoplasm and nucleoplasm of cells. Thus, the system enables an avenue for a more thorough understanding of the mechanisms of microdomain formation for the broad implementation of: tissue engineering pathways through cell encapsulation, protein microdomains as intra- and extracellular switches, protocells as bioreactors, drug delivery vehicles and depots, and fundamental studies of biological macromolecule assembly into condensed phases. Within this paradigm, other materials include: hydrophilic and hydrophobic liquid monomers; synthetic polymers; protein and nucleic acid components; water/polymer and water/monomer mixtures; epoxies; non-polymeric liquids; cells; organelles; viruses; polysaccharides; polymer/monomer combinations; and mixtures thereof.

Figure 6:
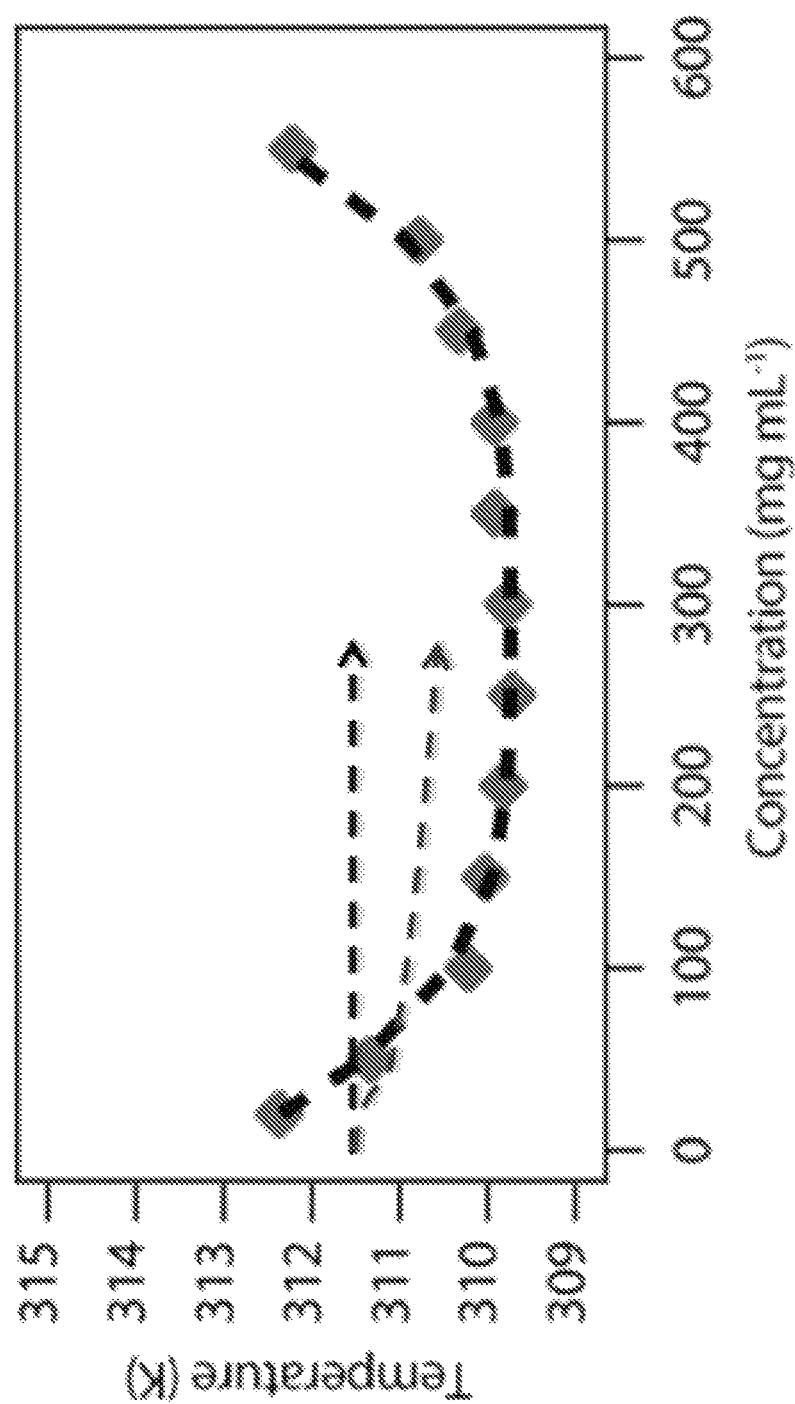
FIG. 6 depicts isothermal and nonisothermal paths from one-phase region to two-phase region on a phase diagram via droplet solvent evaporation according to at least one embodiment of the present disclosure.

FIG. 6 depicts isothermal (top arrow) and nonisothermal (bottom arrow) paths from one-phase region to two-phase region on a phase diagram via droplet solvent evaporation.

Figure 7A:
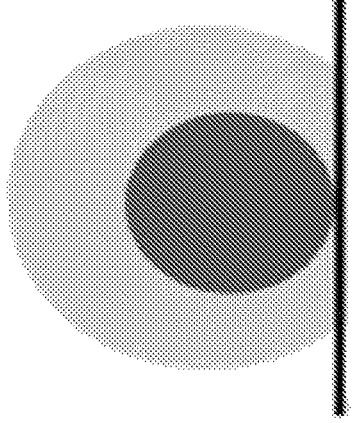
FIGS. 7A-7F depicts structures formed by the droplet evaporation method according to at least one embodiment of the present disclosure.
Figure 7B:
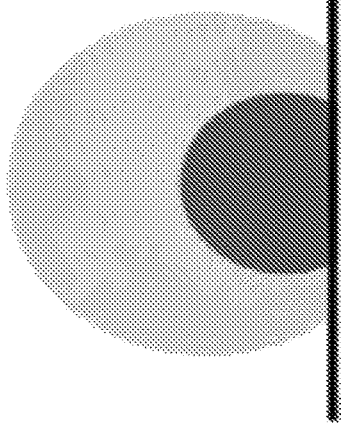
Figure 7C:
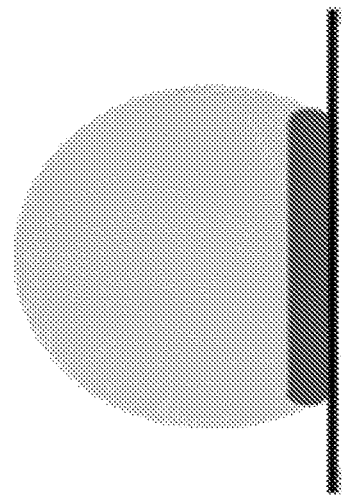
Figure 7D:
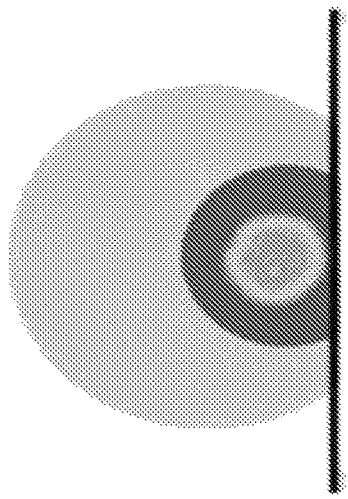
Figure 7E:
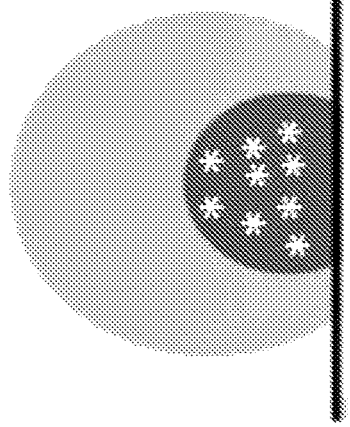
Figure 7F:
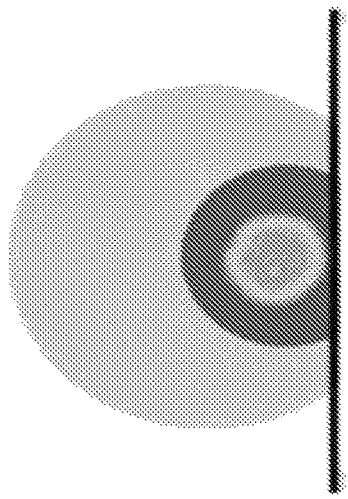
Figure 8:
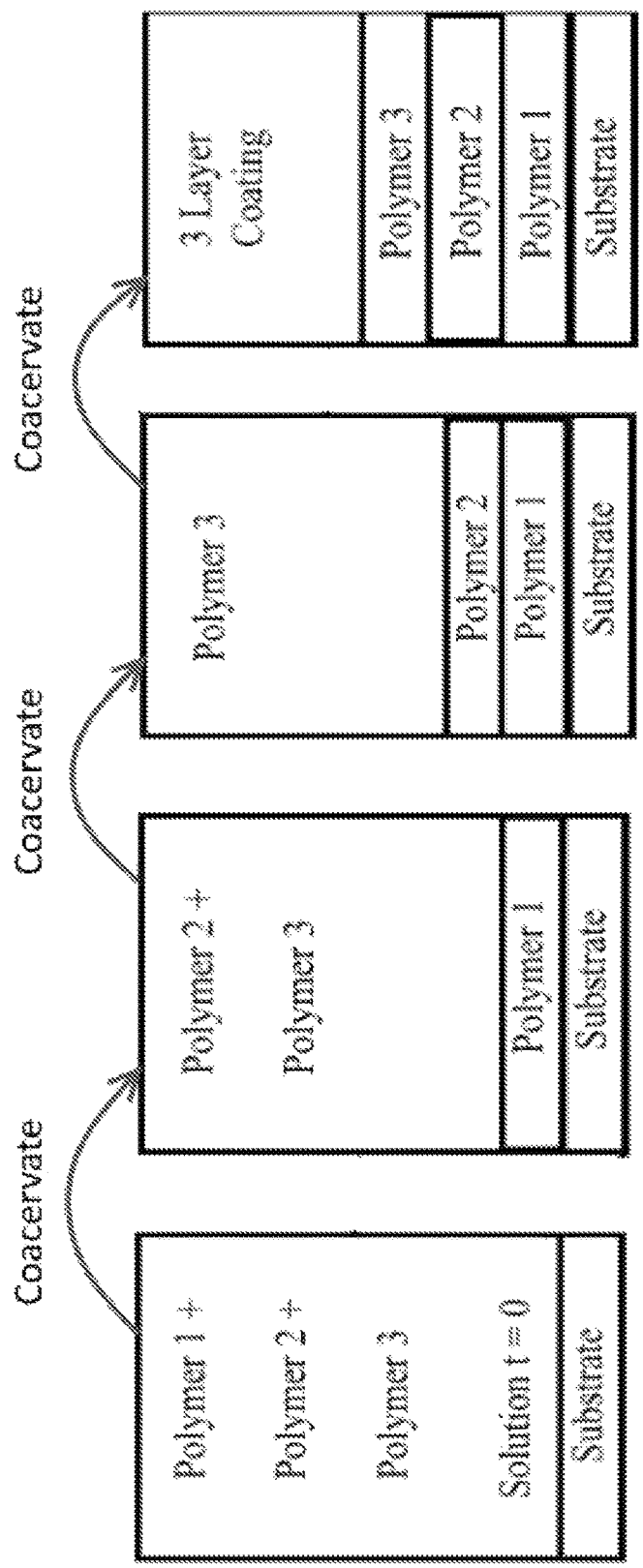
FIG. 8 depicts a schematic illustration of multilayer polymer coacervate coatings according to at least one embodiment of the present disclosure.

In another embodiment, methods are provided for coating a substrate. The substrate can include one or more of a medical device, a stent, a vascular graft, a catheter, a biosensor, a drug reservoir, or a cell culture substrate. Examples of coating of substrates are shown in FIGS. 7-8.

FIGS. 7A-7F depicts structures formed by the droplet evaporation method, including non-wetting (FIG. 7A), partially wetting (FIG. 7B) and fully wetting (FIG. 7C) phase-transitioned coacervates on a substrate surface. Additional structures can include multilayer compartments (FIG. 7D), and micelles or other particles (FIG. 7E) and cells (FIG. 7F) encapsulated within the resultant coacervates.

The approach is not limited to creating hierarchical liquid compartments within emulsions using temperature-induced phase separation. The platform is amenable to evolving the phase-separated structures presented herein within surface-bound drops via controlled evaporation. The strategy is to control evaporation of solvent (e.g., water) from a multi-component droplet to move across the phase diagram from the one-phase region to the two phase region, as shown schematically in FIG. 6. This methodology obviates the requirement of an external continuous fluid (e.g., oil) and provides modulated control of the components via extent of solvent evaporation. The top arrow in FIG. 6 represents the ideal horizontal isothermal path across the phase diagram into the two-phase region. Droplet cooling may occur due to evaporation; the bottom arrow in FIG. 6 represents a pathway whereby phase separation occurs via a non-isothermal evaporative process. In both examples, coacervate formation is expected to occur because the final state of the system falls within the two-phase region of the phase diagram.

The surface chemistry and topography of the substrate is key in determining the properties of the resultant phase-transitioned coacervates. For example, if the coacervate does not wet the surface preferentially to water, a spherical coacervate to form within the drop is expected, as illustrated in FIG. 7A. Surface coatings that can result in this non-wetting behavior include, but are not limited to: PEG-silane, PEG-thiols on gold, POEGMA brushes, and zwitterionic surfaces. In the case of a coacervate contact angle between 0° and 180° with respect to water, the coacervate can achieve formation of a partial sphere (FIG. 7B). If the coacervate completely wets the surface, a uniform film may form at the bottom of the drop upon coacervation (FIG. 7C); this film could be attained by tethering polymers or oligomerss to the surface expressing the same (or similar) physical properties to those in the coacervate. The approach also applies to hierarchical structures evolved within the drops. This fabricatiooin strategy can easily be extended to multilayer compartments (FIG. 7D), coacervates encapsulating micelles and other nano- to micro-particles (FIG. 7E), and cell, organelle or virus encapsulation (FIG. 7F) within the formed coacervates.

Other examples whereby the concepts, methods and materials described supra can be used include the formation of multilayer, blend or micro- and nanostructured thin film coatings on surfaces of solid materials by tailoring the phase behavior and surface interactions of polymers. Of particular interest is the formation of such complex coatings from peptide polymers and other bioactive polymers, which may be tailored to have a number of desirable biological properties for biomedical applications.

Formation of liquid coacervate phases in the form of thin films (coatings) on a desired surface can be accomplished using any of the means described above (temperature change, evaporation, change in solvent quality (e.g. by addition of cosolutes) by placing the surface (e.g. biomedical device) of interest to be coated into a homogeneous solution of the polymer mixtures either before or while phase separation (coacervation) is occurring. FIG. 8 depicts a schematic illustration of multilayer polymer coacervate coatings. In this example, tailoring n constituent phase transitions in multicomponent systems enables formation of n immiscible wetting layers (n=3 above). In other examples, each layer can consist of a single component, immiscible with other components or can consist of blends, where multiple chemically heterogeneous components are tuned to be miscible in the same layer, and combinations thereof.

Morphology of the coating on the surface depends on the sequence of selective coacervation (phase separation) of polymeric components in solution onto the surface of interest, and the wetting behavior of the phase separating polymer on that surface. In analogy to the structures depicted in FIGS. 7A-7C, wetting can determine the lateral morphology of the phase separating layers, so that structures can range from uniformly spread multilayers to poorly spread layers that display a complex topography.

Examples of the types of biomedical devices that can be coated include stents, vascular grafts, catheters, biosensors, cell culture substrata or any material or device for which a biofunctional coating comprising the polymer layer is desired.

Examples of the types of bioactive function for these coatings include, drug delivery, drug elution, cell encapsulation, biosensing, diagnostics, theranostics, permselective membranes, lubrication layers, and templates for biomineralization of other forms of materials self-assembly.

After (or during) formation of the polymer layer by selective coacervation and controlled wetting, it may be necessary to stabilize them by crosslinking, mineralization or otherwise encapsulating them. Crosslinking may be by covalent, coordination, ionic, disulfide and hydrogen bonding for example.

One method for coating a substrate includes stimulating a solution having one or a mixture of components, wherein the substrate is immersed within the solution, and the stimulation induces a phase separation point of a first component. The stimulation is maintained at the phase separation point to form a degree of a coacervate domain of the first component on a surface of the substrate. The degree of coacervate domain formed on the surface is based on the wetting property of the substrate. The stimulating and maintaining is repeated for one or more additional components in the mixture to form a coacervate domain of the additional component(s).

Another method for coating a substrate includes stimulating a population of aqueous droplets in the form of a water-in-oil emulsion where the droplets include a solution of one or a mixture of components. The substrate is immersed within the population of aqueous droplets. Stimulation of the droplets induces a phase separation point of a first component and maintaining stimulation at the phase separation point forms a tunable degree of a coacervate domain of the first component on a surface of the substrate. The tunable degree of the coacervate domain that is formed on the surface is based on the wetting property of the substrate. The stimulating and maintaining is repeated for one or more additional components in the mixture to form a coacervate domain of the additional component(s).

The coated substrates, formed by the methods described herein, can include a grafted molecule present on the surface of the substrate. In this case, the degree of formation of the coacervate domain of the first component, and/or additional components, on the surface of the substrate can be controlled by one or both of the level of interaction of the respective component with the molecule and with the wetting property of the substrate.

The coacervate domain of the first component and the additional component(s) on the surface of the substrate can be in the form of a single layer coacervate domain, a multilayered coacervate domain, a blended alloy coacervate domain, or combinations thereof.

In one embodiment, a coated substrate is provided that is produced by a process including stimulating a solution of one or a mixture of components, wherein a substrate is immersed within the solution, wherein the stimulation induces a phase separation point of a first component; maintaining stimulation at the phase separation point to form a degree of a coacervate domain of the first component on a surface of the substrate based on a wetting property of the substrate; and repeating the stimulating and maintaining for one or more additional components in the mixture to form a coacervate domain of the additional component.

In one embodiment, a coated substrate is provided that is produced by a process including stimulating a population of aqueous droplets in the form of a water-in-oil emulsion, wherein the droplets include a solution of one or a mixture of components, wherein a substrate is immersed within the population of aqueous droplets, and wherein the stimulation induces a phase separation point of a first component; maintaining stimulation at the phase separation point to form a tunable degree of a coacervate domain of the first component on a surface of the substrate based on a wetting property of the substrate; and repeating the stimulating and maintaining for one or more additional components in the mixture to form a coacervate domain of the additional component.

With respect to the methods and processes described herein for formation of nano- to microscale liquid coacervate particles and coated substrates, the methods and processes of formation can further include stabilizing at least an outermost coacervate domain of the droplet or of the outermost coacervate domain on the surface of the substrate. Stabilization can be effected by one or a combination of mineralization or formation of cross-links by one or a combination of covalent coordination, ionic interaction, disulfide bonds, or hydrogen bonds. After stabilization of the outermoset coacervate domain of the liquid droplet, this domain remains consolidated upon cessation of stimulation at the phase separation point for this coacervate domain, and capsule structures are formed. After stabilization of the outermoset coacervate domain on the surface of the substrate, this domain remains consolidated upon cessation of stimulation at the phase separation point for this coacervate domain. In addition to the outermost coacervate domains, one or more of the additional coacervate domains can be stabilized in the droplets and on the substrate surfaces. After stabilization, the coacervate domain(s) can remain consolidated upon cessation of stimulation at the respective phase separation point of the respective component(s) of the domain.

The components of the present methods and processes can include, for example, but are not limited to, a polymer, a synthetic polymer, a hydrophilic polymer, a hydrophobic polymer, an amphiphilic polymer, an amphiphilic diblock polymer, a protein, a nucleic acid, an epoxy, or a polysaccharide, and combinations thereof. The component can include a polymer. The polymer can include a polypeptide. The polypeptide can include at least a portion of an ELP elastin-like polypeptide (ELP).

In some embodiments, any component, or mixture of components can include an attached bioactive agent. The bioactive agent can include one or a combination of: a drug, a protein, a peptide, a peptide hormone, a ligand, a cell-signaling ligand, or an RGD cell binding domain, to cause recruitment of the drug, protein, peptide, peptide hormone, ligand, cell-signaling ligand, or RGD cell binding domain to the coacervate domain of a component. In an embodiment where a component is a polypeptide, the bioactive agent can be attached through an amino acid linkage or through a chemical linkage through a reactive peptide residue. The reactive peptide residue can include, for example, but is not limited to lysine, cysteine, and aspartic acid. The polypeptide attached to the bioactive agent can include a protease cleavage site. In some embodiments, the population of droplets are aqueous and the solution includes one or a combination of a cell, a virus, or a nanoparticle having a coating of at least one component to cause recruitment of the coated cell, virus, or nanoparticle to the coacervate domain of the respective component within each of the droplets.

The phase separation point of any component, or mixture thereof, can be a phase separation temperature. For components or mixtures having a phase separation temperature, the stimulus can include heating. The phase separation point can also include other phase separation characteristics, the characteristics relating to the stimulus applied to affect a phase separation. For example, the stimulation can include: addition or removal of one or more of the components, evaporation of the droplets or solution, controlled diffusion of one or more of the components, electrostatic quenching of one or more of the components, inducing a reaction of one or more of the components, isomerization of one or more of the components, crosslinking of one or more of the component, or crystallization of one or more of the components, and combinations thereof.

In some embodiments of the present disclosure, the solution includes at least one surfactant for controlling a size of one or more coacervate domains. The surfactant can include an amphiphilic diblock polymer. For example, but not limited thereto, a component can be a hydrophobic ELP polymer and the amphiphilic diblock polymer can be an ELP diblock polymer. By changing the ratio of a surfactant to a component, the resulting coacervate domain size can be manipulated. In some embodiments, a ratio of the hydrophobic ELP polymer to the amphiphilic ELP diblock polymer can range from about 1:1 to about 50:1, which can result in the size of an outermost coacervate domain ranging from about 50 nm to about 20 μm.

In at least one embodiment, two or more components can have similar phase separation points. When stimulation induces a phase separation point of the two or more components, a blended alloy coacervate domain can be formed. For example, but not limited thereto, where a first phase separation point of a first component and an additional phase separation point of an additional temperature are each similar phase separation temperatures, and the stimulus includes heating, an alloy coacervate domain can be formed. The coacervate domains of the various components can form a multilayered coacervate domain, a blended alloy coacervate domain, or a combination thereof.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

REFERENCES

1. Hyman, A. A. & Simons, K. Beyond Oil and Water—Phase Transitions in Cells. *Science* 337, 1047-1049, doi: 10.1126/science. 1223728 (2012).
2. Lingwood, D. & Simons, K. Lipid Rafts As a Membrane-Organizing Principle. *Science* 327, 46-50, doi:10.1126/science. 1174621 (2010).
3. Strulson, C. A., Molden, R. C., Keating, C. D. & Bevilacqua, P. C. RNA catalysis through compartmentalization. *Nat Chem* 4, 941-946, doi:http://www.nature.com/nchem/journal/v4/n 11/abs/nchem. 1466.html—supplementary-information (2012).
4. Dewey, D. C., Strulson, C. A., Cacace, D. N., Bevilacqua, P. C. & Keating, C. D. Bioreactor droplets from liposome-stabilized all-aqueous emulsions. *Nat Commun* 5, doi: 10.1038/ncomms5670 (2014).
5. Wang, W. et al. Hole-Shell Microparticles from Controllably Evolved Double Emulsions. *Angewandte Chemie International Edition* 52, 8084-8087, doi:10.1002/anie.201301590 (2013).
6. Kim, S.-H., Abbaspourrad, A. & Weitz, D. A. Amphiphilic Crescent-Moon-Shaped Microparticles Formed by Selective Adsorption of Colloids. *Journal of the American Chemical Society* 133, 5516-5524, doi:10.1021/ja200139w (2011).
7. Caruso, F. & Möhwald, H. Protein Multilayer Formation on Colloids through a Stepwise Self-Assembly Technique. *J Am Chem Soc* 121, 6039-6046, doi:10.1021/ja990441m (1999).
8. Hartgerink, J. D., Beniash, E. & Stupp, S. I. Peptide-amphiphile nanofibers: A versatile scaffold for the preparation of self-assembling materials. *Proceedings of the National Academy of Sciences* 99, 5133-5138, doi: 10.1073/pnas.072699999 (2002).
9. Chen, J. & Seeman, N. C. Synthesis from DNA of a molecule with the connectivity of a cube. *Nature* 350, 631-633 (1991).
10. Andersen, E. S. et al. Self-assembly of a nanoscale DNA box with a controllable lid. *Nature* 459, 73-76, doi: 10.1038/nature07971 (2009).
11. Dreher, M. R. et al. Temperature triggered self-assembly of polypeptides into multivalent spherical micelles. *J Am Chem Soc* 130, 687-694, doi:10.1021/ja0764862 (2008).
12. Enoch, H. G. & Strittmatter, P. Formation and Properties of 1000-angstrom-Diameter, Single-Bilayer Phospholipid Vesicles. *P Natl Acad Sci USA* 76, 145-149, doi:10.2307/69449 (1979).
13. Utada, A. S. et al. Monodisperse Double Emulsions Generated from a Microcapillary Device. *Science* 308, 537-541, doi:10.2307/3841301 (2005).
14. Chu, L.-Y., Utada, A. S., Shah, R. K., Kim, J.-W. & Weitz, D. A. Controllable Monodisperse Multiple Emulsions. *Angewandte Chemie International Edition* 46, 8970-8974, doi:10.1002/anie.200701358 (2007).
15. Nie, Z., Li, W., Seo, M., Xu, S. & Kumacheva, E. Janus and Ternary Particles Generated by Microfluidic Synthesis: Design, Synthesis, and Self-Assembly. *J Am Chem Soc* 128, 9408-9412, doi:10.1021/ja060882n (2006).
16. Meyer, D. E. & Chilkoti, A. Purification of recombinant proteins by fusion with thermally-responsive polypeptides. *Nat Biotech* 17, 1112-1115 (1999).
17. Torza, S. & Mason, S. G. Three-phase interactions in shear and electrical fields. *Journal of Colloid and Interface Science* 33, 67-83, doi:http://dx.doi.org/10.1016/0021-9797(70)90073-1 (1970).

The invention claimed is:

1. A method for forming multi-phased coacervate particles comprising:
    providing an aqueous solution comprising a plurality of polymers, wherein the plurality of polymers are miscible in the solution under a first set of conditions and wherein the plurality of polymers comprises
        a first polymer that undergoes phase separation upon a change in solution conditions, wherein the first polymer is a hydrophobic homopolymeric elastin-like polymer (ELP), and
        a second polymer that undergoes phase separation upon a change in solution conditions, the second polymer comprising an amphiphilic diblock homopolymeric polymer (ELP), wherein the second polymer is a different polymer than the first polymer; and
    altering the solution conditions so that the first and second polymers become immiscible and undergo phase separation and form the multi-phased coacervate particles each comprising at least two, separated, immiscible phases with defined structure, wherein the multi-phased coacervate particles each comprise a coacervate domain having a size of about 50 nm to 20 microns.

2. The method of claim 1 wherein the multi-phased coacervate particle comprises a core-shell architecture.

3. The method of claim 1 wherein the multi-phased structure comprises a structure other than a core-shell architecture.

4. The method of claim 1 wherein the first and second phase separations take place sequentially in time.

5. The method of claim 1 wherein the multi-phased coacervate particle comprises a Janus structure.

6. The method of claim 1 wherein altering the conditions comprises altering the temperature of the solution.

7. The method of claim 1 wherein altering the conditions comprises evaporation.

8. The method of claim 1 wherein altering the conditions comprises changing the solvent quality comprising adding a cosolute to the solution.

9. The method of claim 1 wherein the first and second polymers are thermally-responsive ELPs and altering the conditions comprises altering the temperature of the solution.

10. The method of claim 1 wherein the plurality of polymers comprises a third polymer that is miscible in the solution under the first set of conditions and which undergoes phase separation upon a change in solution conditions, the method further comprising:
    altering the conditions so that the third polymer is immiscible in the solution and undergoes phase separation to form at least a third, separated, immiscible phase with defined structure.

11. The method of claim 1 wherein the plurality of polymers comprises n polymers, where n is a number, that are miscible in the solution under the first set of conditions, each capable of undergoing phase separation upon a change in solution conditions, the method further comprising altering the conditions up to n number of times to form a number of immiscible phases in the solution.

12. The method of claim 11 wherein the step of altering the conditions comprises heating the solution.

13. The method of claim 1 wherein the plurality of polymers comprises at least two polymers that undergo coacervation at the same time and thus form a blended alloy coacervate domain.

14. The method of claim 1 further comprising providing a substrate wherein the polymers coacervate on the surface of the substrate.

15. The method of claim 1 wherein the solution further comprises a bioactive agent.

16. The method of claim 12 wherein the bioactive agent is selected from the group consisting of a drug, a protein, a peptide, a peptide hormone, a ligand, a cell-signaling; ligand, and an RGD cell binding domain.

17. The method of claim 1 wherein a bioactive agent is attached to at least one of the polymers.

18. The method of claim 14 wherein the bioactive agent is selected from the group consisting of a drug, a protein, a peptide, a peptide hormone, a ligand, a cell-signaling ligand, and an RGD cell binding domain.

19. The method of claim 1, further comprising crosslinking at least one of the resulting phase separated structures to form a gel containing material.

20. The method of claim 1 wherein altering the conditions comprises in-situ chemical and physical modification of solution polymers.

21. The method of claim 20 wherein the chemical modification is selected from (de)methylation or (de)phosphorylation of a polypeptide, click chemistry to (i) attach small chemical moieties or (ii) increase the degree of polymerization via concatenation of polymers.

22. The method of claim 1, wherein a mole ratio of the hydrophobic homopolymeric ELP to the amphiphilic diblock homopolymeric ELP is about 1:1 to about 50:1.

* * * * *

UNITED STATES PATENT AND TRADEMARK OFFICE
CERTIFICATE OF CORRECTION

PATENT NO. : 11,583,819 B2
APPLICATION NO. : 16/817299
DATED : February 21, 2023
INVENTOR(S) : Lopez et al.

It is certified that error appears in the above-identified patent and that said Letters Patent is hereby corrected as shown below:

On the Title Page

On page 2, in Column 1, under "Other Publications", Line 23, delete "controilabie" and insert --controllable-- therefor On page 2, in Column 1, under "Other Publications", Line 32, delete "ali-aqueous" and insert --all-aqueous-- therefor In the Claims In Column 18, Line 20, in Claim 1, after "comprises", insert --:--

In Column 18, Line 27, in Claim 1, after "homopolymeric", insert --elastin-like--

In Column 19, Line 20, in Claim 16, delete "cell-signaling;" and insert --cell-signaling-- therefor Signed and Sealed this
Thirteenth Day of February, 2024

Katherine Kelly Vidal
*Director of the United States Patent and Trademark Office*